(12) United States Patent
Mou et al.

(10) Patent No.: US 11,204,304 B2
(45) Date of Patent: *Dec. 21, 2021

(54) GAS DETECTING DEVICE

(71) Applicant: Microjet Technology Co., Ltd., Hsinchu (TW)

(72) Inventors: Hao-Jan Mou, Hsinchu (TW); Chi-Feng Huang, Hsinchu (TW); Yung-Lung Han, Hsinchu (TW); Chang-Yen Tsai, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 357 days.

This patent is subject to a terminal disclaimer.

(21) Appl. No.: 16/233,864

(22) Filed: Dec. 27, 2018

(65) Prior Publication Data

US 2019/0234840 A1  Aug. 1, 2019

(30) Foreign Application Priority Data

Jan. 31, 2018 (TW) ................. 107103539

(51) Int. Cl.
*G01N 1/24* (2006.01)
*G01N 1/22* (2006.01)
*G01N 33/00* (2006.01)

(52) U.S. Cl.
CPC ............ *G01N 1/24* (2013.01); *G01N 1/2273* (2013.01); *G01N 33/004* (2013.01);
(Continued)

(58) Field of Classification Search
None
See application file for complete search history.

(56) References Cited

U.S. PATENT DOCUMENTS 10,921,221 B2 * 2/2021 Mou ................... G01N 33/0047
10,955,319 B2 * 3/2021 Mou .................... G01N 33/004
(Continued)

FOREIGN PATENT DOCUMENTS

CN  201600359 U  10/2010
CN  203798727 U  8/2014
(Continued)

OTHER PUBLICATIONS

Lafond, A., "List of Common Volatile Organic Compunds (VOCs)", Foobot, May 21, 2021, pp. 1-4.*
(Continued)

*Primary Examiner* — Daniel S Larkin
(74) *Attorney, Agent, or Firm* — Birch, Stewart, Kolasch & Birch, LLP

(57) ABSTRACT

A gas detecting device includes a casing, at least one gas transporting actuator, at least one valve and at least one external sensor. The casing has an airflow chamber, an inlet, a branch channel and a connection channel. The airflow chamber communicates with the exterior of the casing through the inlet, and the branch channel communicates with the airflow chamber and the connection channel. The gas transporting actuator is disposed within the branch channel for transporting air into the airflow chamber and the branch channel from the inlet. The valve is disposed between the connection channel and the branch channel for controlling the air to flow into the connection channel. The external sensor is detachably disposed within the connection channel and has a sensor for measuring the air in the connection channel.

19 Claims, 17 Drawing Sheets

(52) U.S. Cl.
CPC ..... *G01N 33/0004* (2013.01); *G01N 33/0009* (2013.01); *G01N 33/0022* (2013.01); *G01N 33/0047* (2013.01); *G01N 33/0063* (2013.01); *G01N 33/0073* (2013.01)

(56) References Cited

U.S. PATENT DOCUMENTS

| | | |
|---|---|---|
| 2010/0229658 A1 | 9/2010 | Glezer et al. |
| 2012/0143515 A1* | 6/2012 | Norman ............. G01N 33/0031 702/24 |
| 2014/0377099 A1 | 12/2014 | Hsueh et al. |
| 2016/0153884 A1* | 6/2016 | Han .................... G01N 1/2205 73/1.06 |
| 2016/0223437 A1 | 8/2016 | Ajay et al. |
| 2016/0245714 A1 | 8/2016 | Gagne et al. |
| 2016/0327416 A1 | 11/2016 | Gagne et al. |

FOREIGN PATENT DOCUMENTS

| | | |
|---|---|---|
| CN | 205027719 U | 2/2016 |
| CN | 106226355 A | 12/2016 |
| CN | 106233119 A | 12/2016 |
| CN | 206251548 U | 6/2017 |
| TW | M553417 U | 12/2017 |
| TW | M553762 U | 1/2018 |
| TW | M554513 U | 1/2018 |

OTHER PUBLICATIONS

Extended European Search Report dated Jul. 24, 2019, for European Patent Application No. 19150993.4.

* cited by examiner

US 11,204,304 B2

GAS DETECTING DEVICE

FIELD OF THE DISCLOSURE

The present disclosure relates to a gas detecting device, and more particularly to a gas detecting device having a gas transporting actuator for gas transportation.

BACKGROUND OF THE DISCLOSURE

Nowadays, the air pollution problems are becoming increasingly serious in our country and its neighboring regions. There are many harmful gases in daily life. If it fails to be detected in time, it will affect the health of the human body.

Moreover, there are different demands of gas detection for users in different places (e.g., factories, offices or homes). For example, gas sensors for detecting volatile gases or toxic gases causing inhalation injuries are suitably used in factories. Carbon monoxide sensors, carbon dioxide sensors, temperature sensors or humidity sensors are suitably used in homes and offices. Since the commercially available gas detecting device is an integral gas detecting device, some drawbacks occur. For example, the type of the gas to be detected has been determined before the gas detecting device leaves the factory and cannot be changed by the users according to the particle requirements. In that, a gas detecting device cannot provide complete detections to meet the requirements of users. Therefore, there is a need of providing a gas detecting device capable of performing gas detection according to different requirements to address the above-mentioned issues.

SUMMARY OF THE DISCLOSURE

An object of the present disclosure is to provide a gas detecting device having an external sensor for detecting air and providing users with timely and accurate air information. The external sensor of the gas detecting device can be selected and matched according to the requirements of the users. It benefits to achieve the purposes of easy replacement and improving practicality and convenience.

In accordance with an aspect of the present disclosure, a gas detecting device is provided. The gas detecting device includes a casing, at least one gas transporting actuator, at least one valve and at least one external sensor. The casing has an airflow chamber, at least one inlet, at least one branch channel and at least one connection channel. The airflow chamber is in fluid communication with the exterior of the casing through the at least one inlet, the at least one branch channel is in fluid communication with the at least one airflow chamber, and the at least one connection channel is in fluid communication with the at least one branch channel. The at least one gas transporting actuator is disposed on the at least one branch channel and is actuated to inhale air into the at least one airflow chamber through the at least one inlet and transport the air into the at least one branch channel. The at least one valve is disposed between the at least one connection channel and the at least one branch channel to control the air to flow into the at least one connection channel. The at least one external sensor is detachably assembled in the at least one connection channel and includes a sensor to measure the air in the at least one connection channel.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
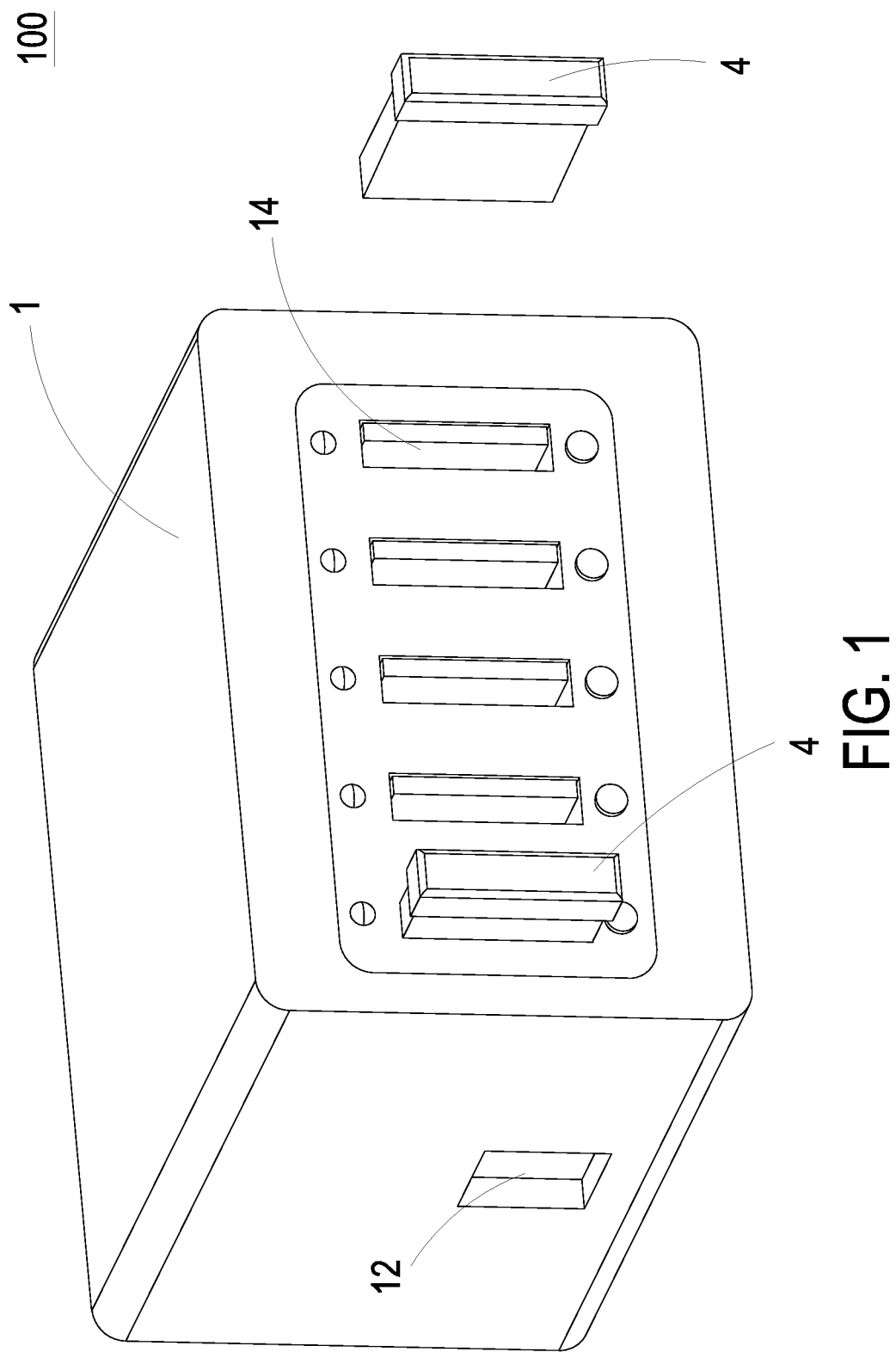
FIG. 1 is a schematic perspective view illustrating a gas detecting device according to an embodiment of the present disclosure.
Figure 2:
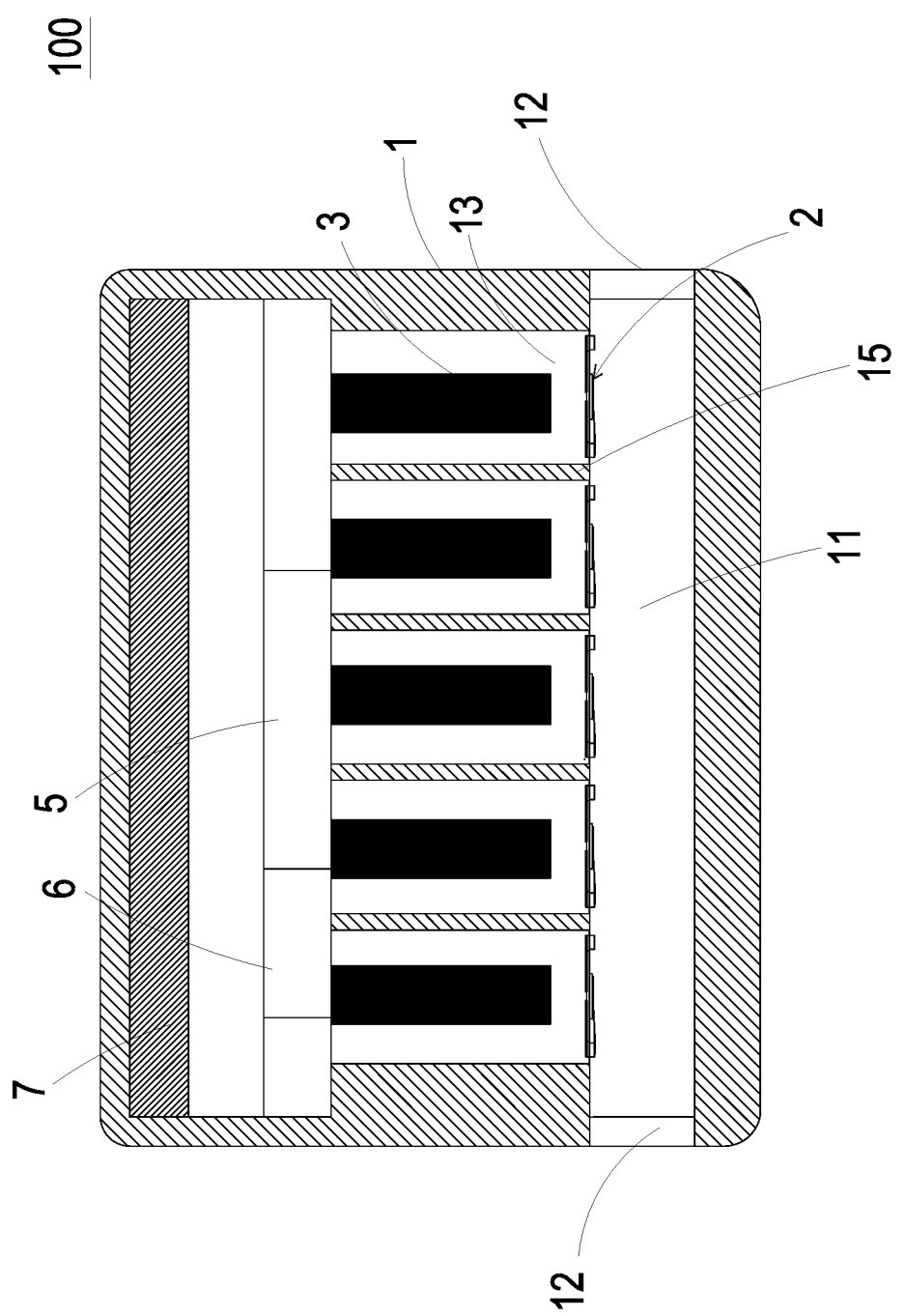
FIG. 2 is a schematic cross-sectional view illustrating the gas detecting device of FIG. 1.

Please refer to FIGS. 1 and 2. The present disclosure provides a gas detecting device 100 including at least one casing 1, at least one gas transporting actuator 2, at least one valve 3, at least one external sensor 4, at least one airflow chamber 11, at least one inlet 12, at least one branch channel 13, at least one connection channel 14 and at least one sensor. The numbers of the casing 1, the airflow chamber 11 and the sensor are exemplified by one for each respectively in the following embodiments but not limited thereto. It is noted that each of the casing 1, the airflow chamber 11 and the sensor can also be provided in plural numbers.

The present disclosure provides a gas detecting device. Please refer to FIGS. 1 and 2. In the embodiment, the gas detecting device 100 includes a casing 1, at least one gas transporting actuator 2, at least one valve 3 and at least one external sensor 4. The casing 1 has an airflow chamber 11, at least one inlet 12, at least one branch channel 13 and at least one connection channel 14. The numbers of the branch channels 13, the connection channels 14, the gas transporting actuators 2 and the valves 3 are corresponding to each other, respectively. The numbers of the branch channels 13, the connection channels 14, the gas transporting actuators 2 and the valves 3 are exemplified by five for each respectively in the following embodiments but not limited thereto. The airflow chamber 11 is in fluid communication with the exterior of the casing 1 through the at least one inlet 12 and in fluid communication with the five branch channels 13. The casing 1 includes a plurality of partition plates 15. The plurality of partition plates 15 are used to space apart the five branch channels 13 and the five connection channels 14. The five connection channels 14 are corresponding in number and positions to and in fluid communication with the five branch channels 13. The five gas transporting actuators 2 are correspondingly disposed on the five branch channels 13, respectively, to transport air contained in the airflow chamber 11 into the corresponding branch channel 13. The five valves 3 are correspondingly disposed in the five connection channels 14 to control the air to flow into the corresponding connection channel 14. Moreover, the five external sensors 4 are detachably assembled in the five corresponding connection channels 14. Each external sensor 4 includes a sensor (not shown) disposed therein. In the embodiment, the sensor of the external sensor 4 can be at least one selected from the group consisting of an oxygen sensor, a carbon monoxide sensor, a carbon dioxide sensor and combinations thereof. In an embodiment, the sensor of the external sensor 4 can be a volatile organic compound sensor. Alternatively, the sensor of the external sensor 4 can be at least one selected from the group consisting of a bacterial sensor, a virus sensor, a microorganism sensor and combinations thereof. Alternatively, the sensor of the external sensor 4 can be at least one selected form the group consisting of a temperature sensor, a humidity sensor and combinations thereof. In that, the sensor of the external sensor 4 is used to detect the air contained in the connection channels 14.

Figure 3A:
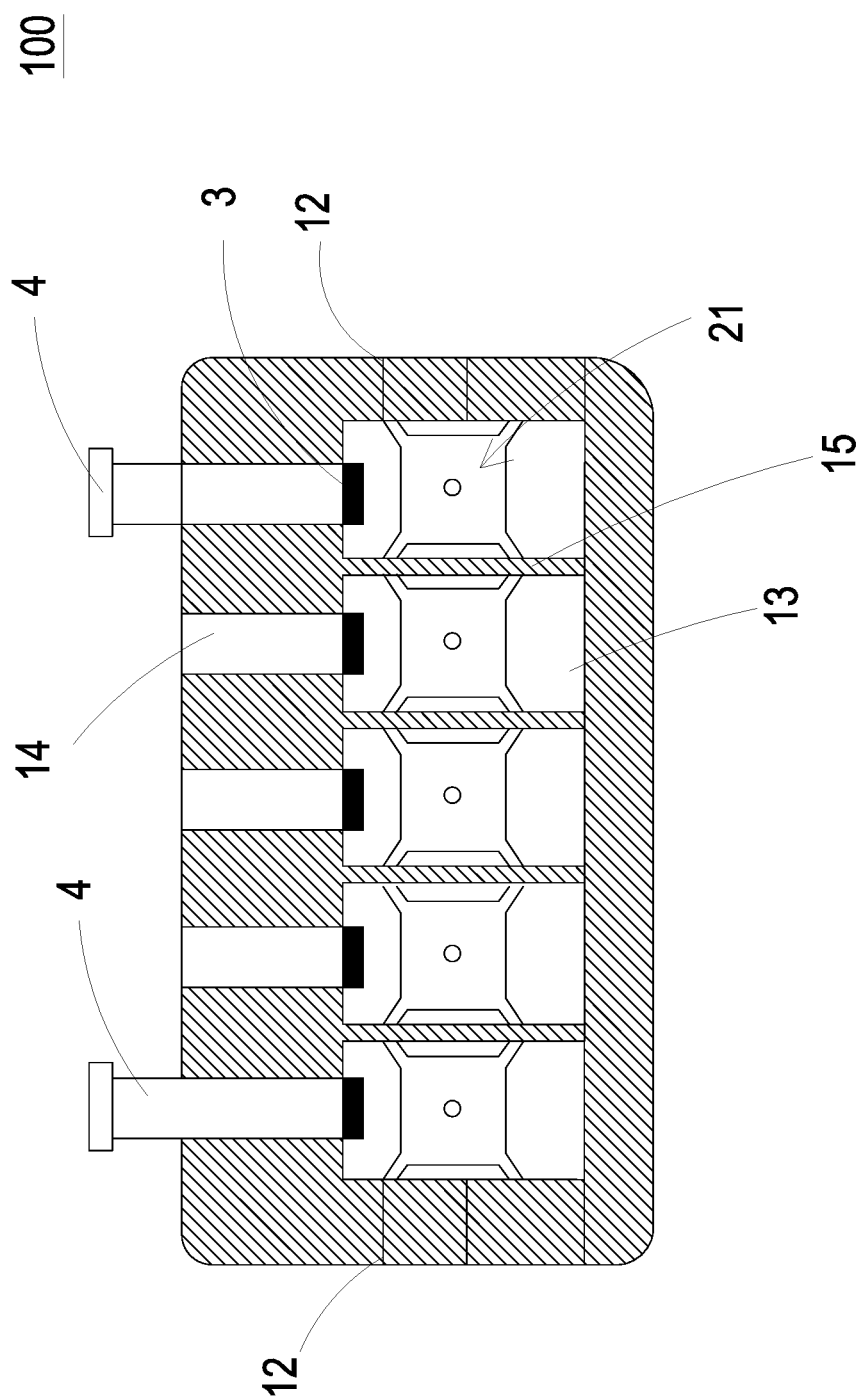
FIG. 3A is a schematic cross-sectional view illustrating a gas transporting actuator of a gas detecting device according to a first embodiment of the present disclosure.
Figure 3B:
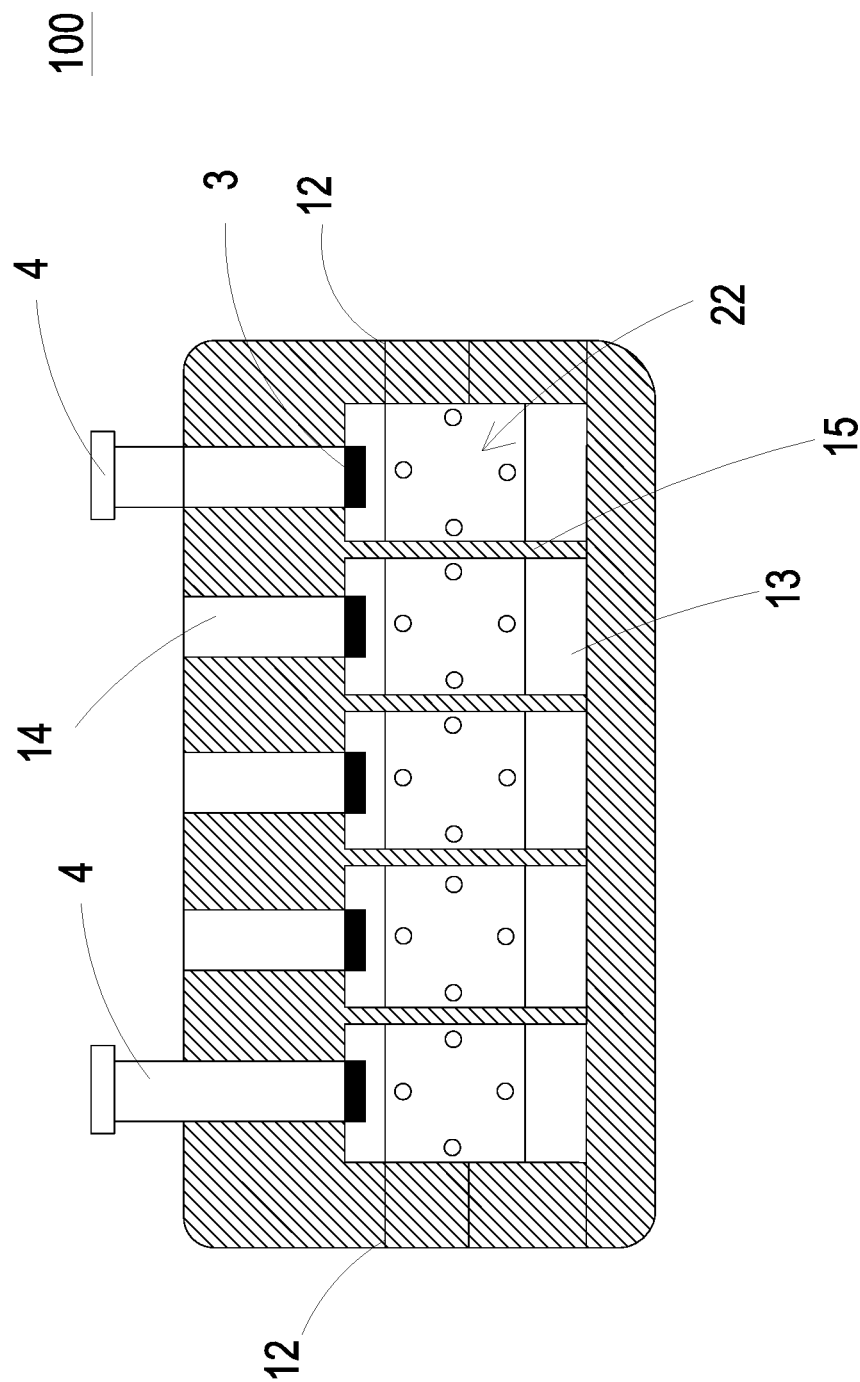
FIG. 3B is a schematic cross-sectional view illustrating a gas transporting actuator of a gas detecting device according to a second embodiment of the present disclosure.

In the embodiment, the gas transporting actuator 2 can be a piezoelectric blower actuator or a piezoelectric actuator. In the following embodiments, FIG. 3A illustrates a gas transporting actuator according a first embodiment of the present disclosure, which is a piezoelectric blower and indicated by 21. Alternatively, FIG. 3B illustrates a gas transporting actuator according a second embodiment of the present disclosure, which is a piezoelectric actuator and indicated by 22.

Figure 4:
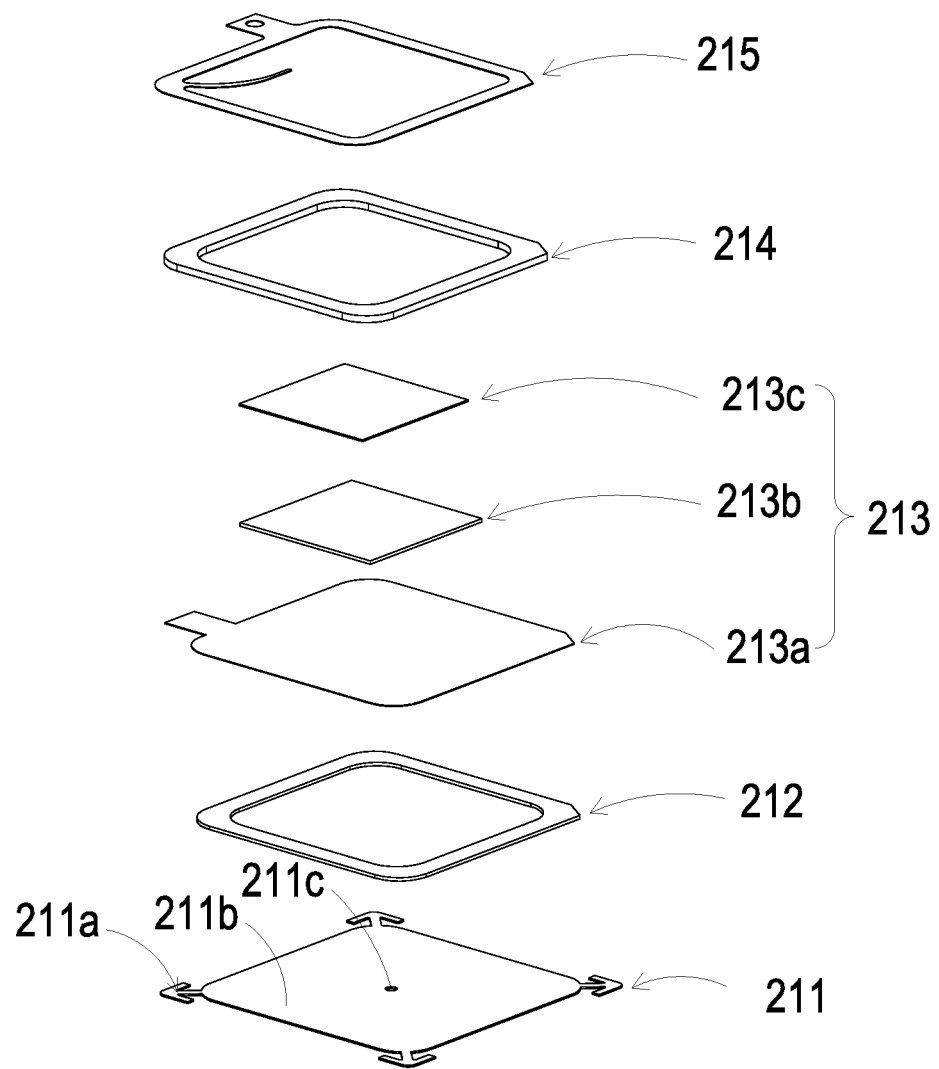
FIG. 4 is an exploded view illustrating the gas transporting actuator according to the first embodiment of the present disclosure.
Figure 5A:
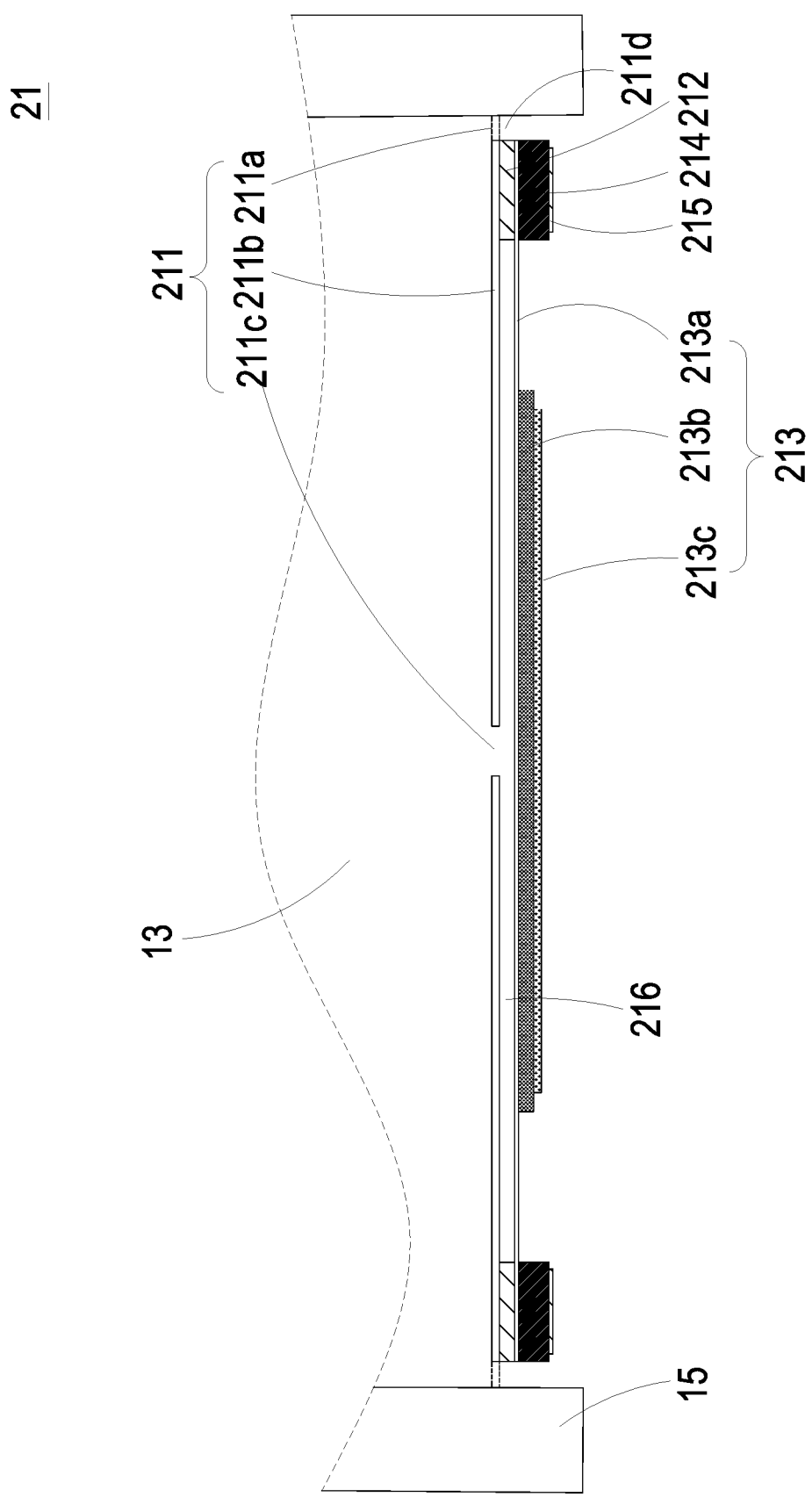
FIG. 5A is a schematic cross-sectional view illustrating the gas transporting actuator of FIG. 4.
Figure 5B:
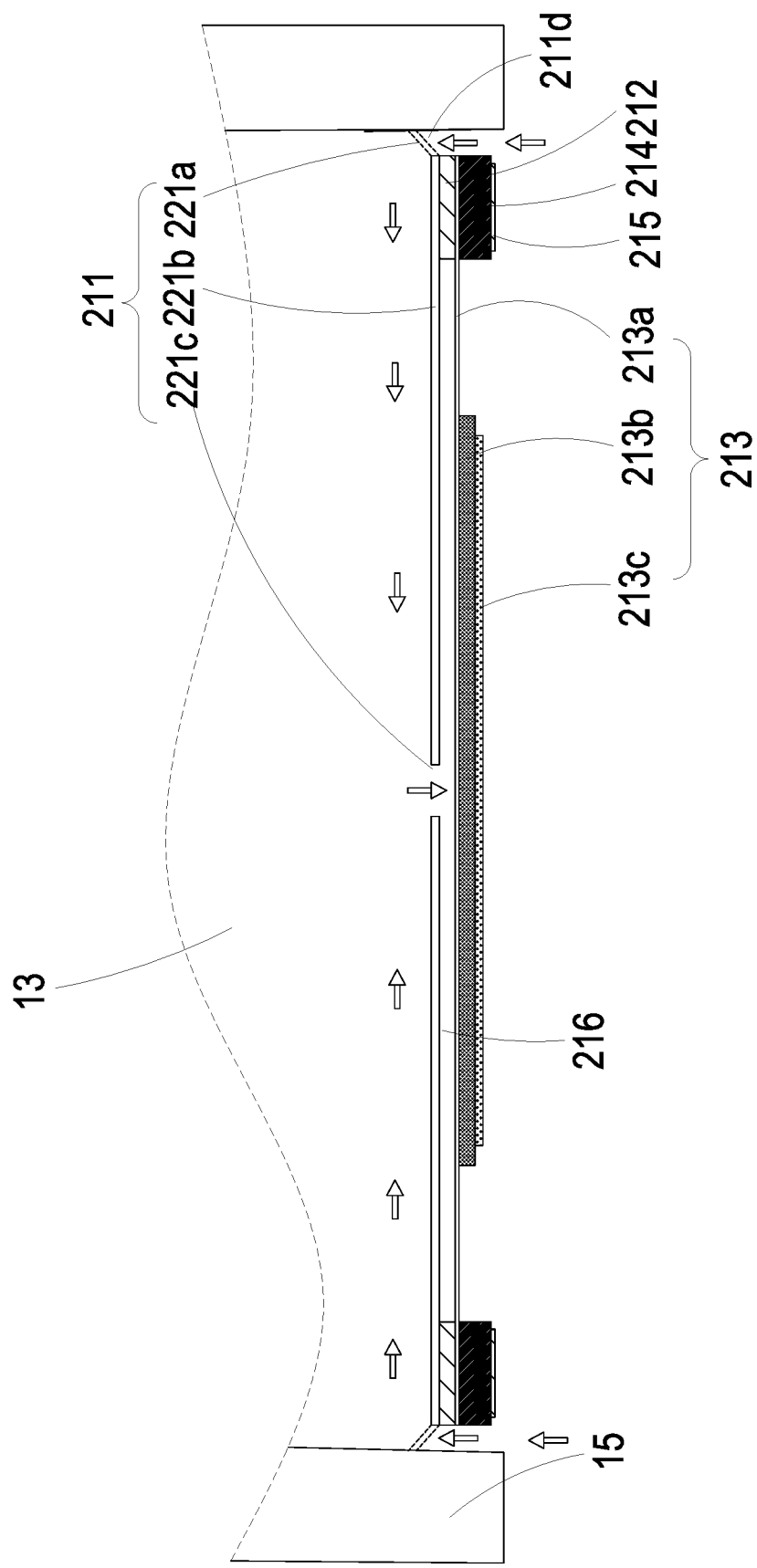
FIG. 5B and FIG. 5C are schematic views illustrating actions of the gas transporting actuator of FIG. 5A.
Figure 5C:
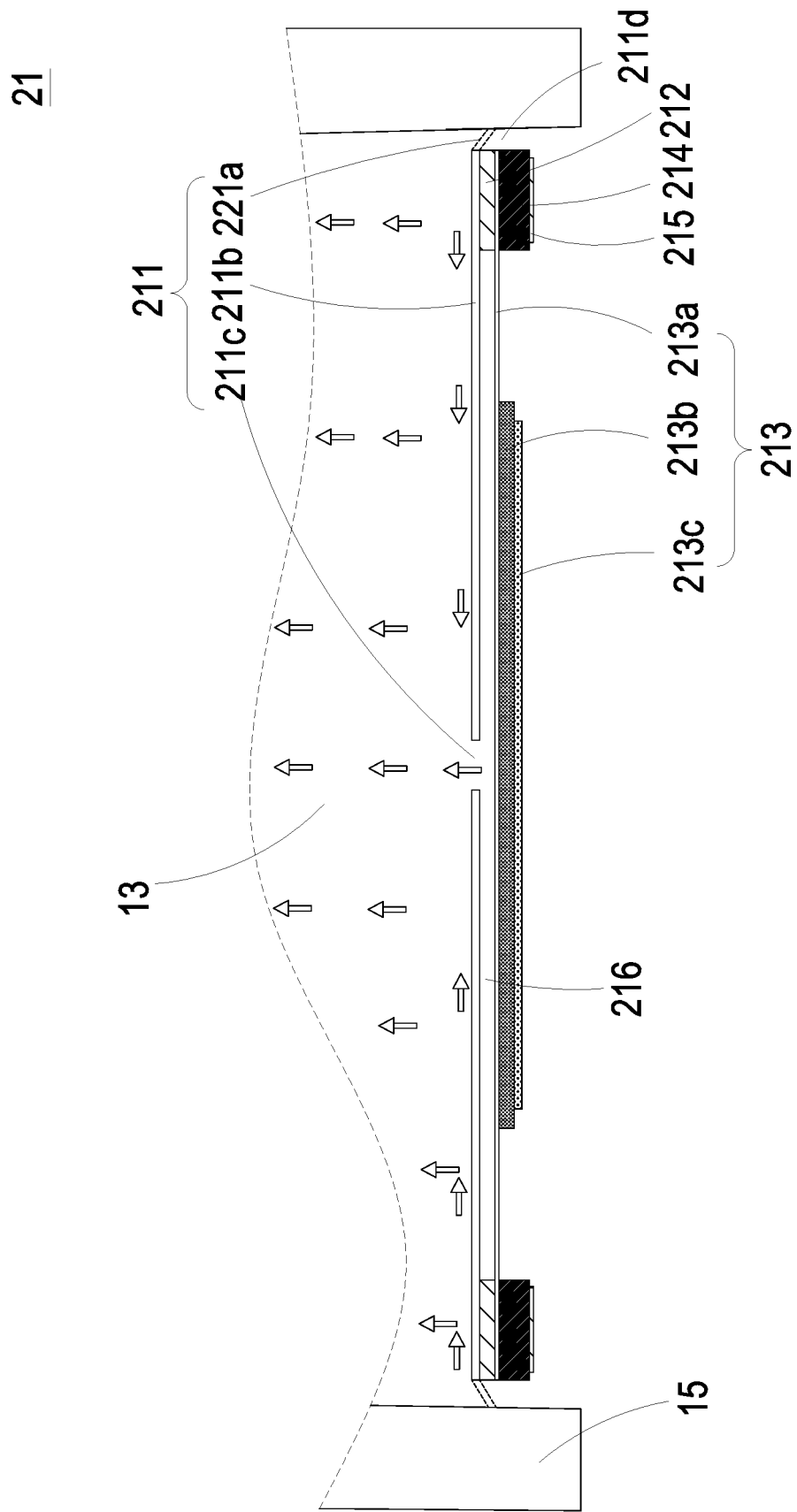

Please refer to FIGS. 3A, 4 and 5A to 5C. FIG. 4 is an exploded view illustrating the gas transporting actuator according to the first embodiment of the present disclosure. FIG. 5A is a schematic cross-sectional view illustrating the gas transporting actuator of FIG. 4. FIG. 5B and FIG. 5C are schematic views illustrating actions of the gas transporting actuator of FIG. 5A. In the embodiment, the gas transporting actuator 21 includes a nozzle plate 211, a chamber frame 212, an actuator 213, an insulation frame 214 and a conducting frame 215 stacked on each other sequentially. The nozzle plate 211 includes a plurality of brackets 211a, a suspension plate 211b, a central aperture 211c and at least one vacant space 211d. The suspension plate 211b is permitted to undergo a bending vibration. The plurality of brackets 211a are connected to the periphery of the suspension plate 211b. In the embodiment, there are four brackets 211a, which are connected to four corners of the suspension plate 211b, respectively, but the present disclosure is not limited thereto. The suspension plate 211b is sleeved and fixed on the partition plate 15 through the plurality of brackets 211a. Consequently, the nozzle plate 211 is positioned and accommodated within the corresponding branch channel 14. The central aperture 211c is formed at the center of the suspension plate 211b, and the vacant spaces 211d are airflow apertures formed among the plurality of brackets 211a. The chamber frame 212 is carried and stacked on the suspension plate 211b. The actuator 213 is carried and stacked on the chamber frame 212 and includes a piezoelectric carrying plate 213a, an adjusting resonance plate 213b and a piezoelectric plate 213c. The piezoelectric carrying plate 213a is carried and stacked on the chamber frame 212. The adjusting resonance plate 213b is carried and stacked on the piezoelectric carrying plate 213a. The piezoelectric plate 213c is carried and stacked on the adjusting resonance plate 213b. As the piezoelectric plate 213c is actuated by an applied voltage, the piezoelectric plate 213c deforms to drive the piezoelectric carrying plate 213a and the adjusting resonance plate 213b to bend and vibrate in the reciprocating manner. The insulation frame 214 is carried and stacked on the piezoelectric carrying plate 213a of the actuator 213. The conducting frame 215 is carried and stacked on the insulation frame 214. A resonance chamber 216 is defined by the actuator 213, the chamber frame 212 and the suspension plate 211b collaboratively. The adjusting resonance plate 213b is thicker than the piezoelectric carrying plate 213a.

Please refer to FIG. 5B. When the piezoelectric plate 213c of the actuator 213 is actuated by an applied voltage, the piezoelectric plate 213c of the actuator 213 is deformed by the piezoelectric effect, and the adjusting resonance plate 213b and the piezoelectric carrying plate 213a are simultaneously driven to vibrate. Thereby, the nozzle plate 211 is driven to move due to the Helmholtz resonance effect, and the actuator 213 is displaced downwardly. Since the actuator 213 is displaced downwardly, the volume of the branch channel 13 is expended and the air contained in the airflow chamber 11 is transported into the branch channel 13 through the vacant spaces 211d formed among the plurality of brackets 211a of the nozzle plate 211 due to the pressure gradient, and further transported into the resonance chamber 216 through the central aperture 211c. As shown in FIG. 5C, the air flows into the branch channel 13 continuously. At the meantime, the actuator 213 is driven to vibrate upwardly in response to the applied voltage, the volume of the branch channel 13 is shrunken. The air is compressed to flow into the connection channel 14 and the air contained in the resonance chamber 216 is ejected out through the central aperture 211c. Consequently, the air is provided to the sensor of the external sensor 4 for detecting. By the gas transporting actuator 21, the air is inhaled from the exterior of the casing 1 through the inlet 12, and the air contained in the airflow chamber 11 can be further transported into the branch channel 13 and the connection channel 14 continuously. Thus, the air contained in the connection channel 14 is provided to the external sensor 4 to detect a specific gas compound.

Figure 6A:
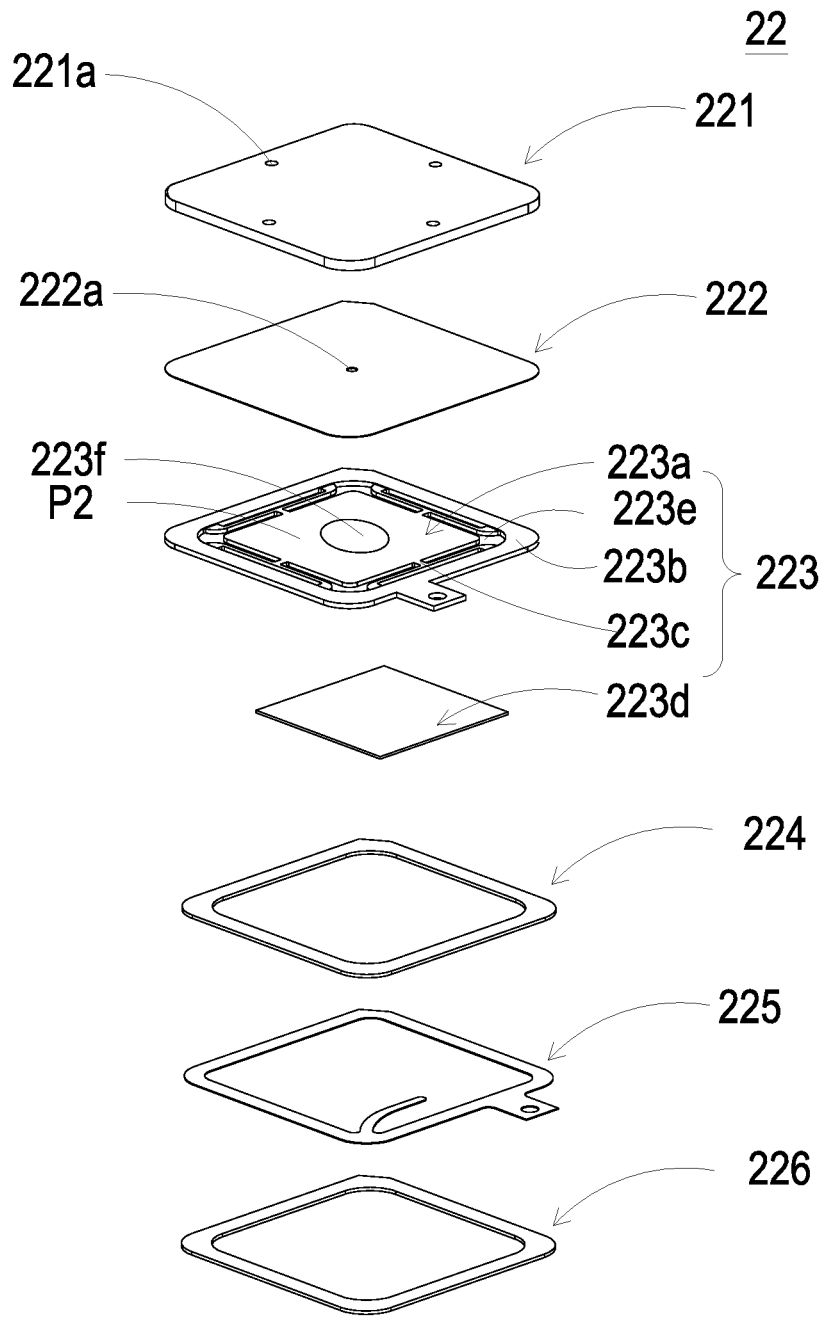
FIG. 6A is an exploded view illustrating the gas transporting actuator according to the second embodiment of the present disclosure and taken from top side.
Figure 6B:
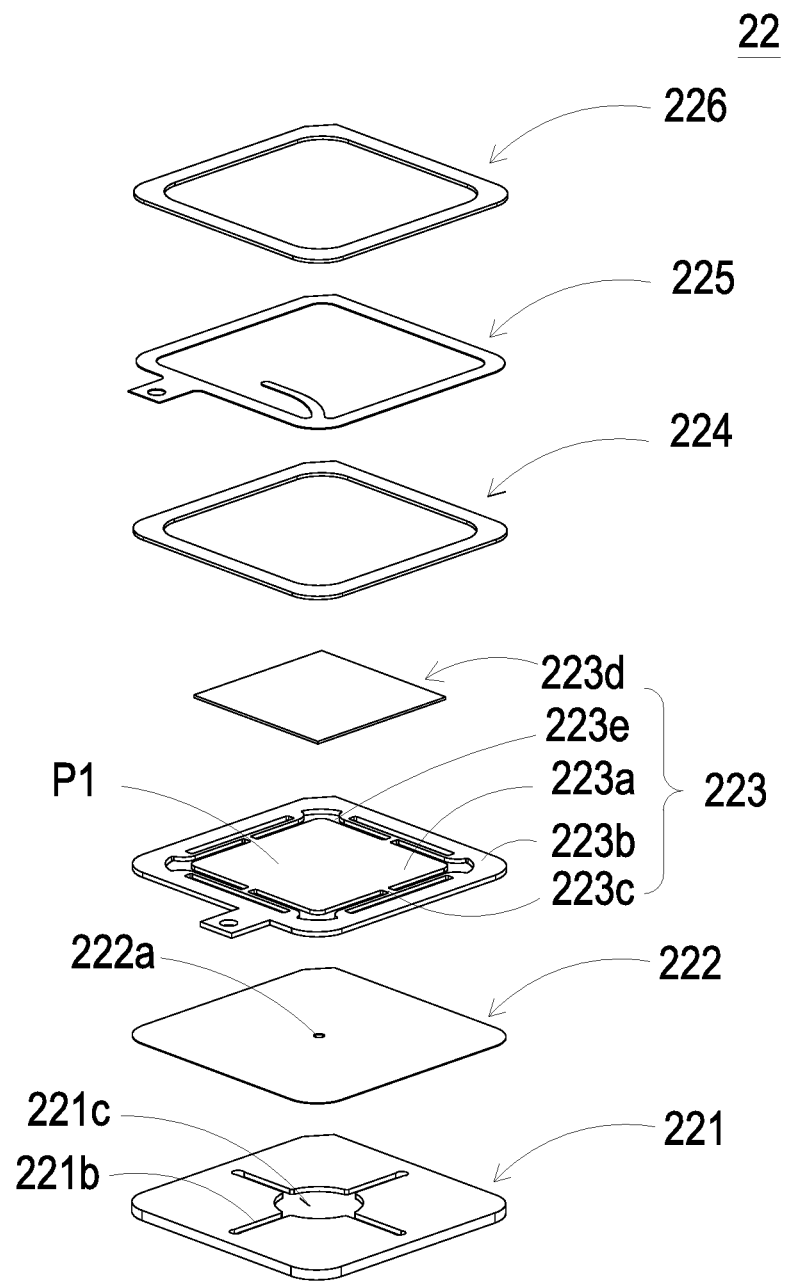
FIG. 6B is an exploded view illustrating the gas transporting actuator according to the second embodiment of the present disclosure and taken from bottom side.
Figure 7A:
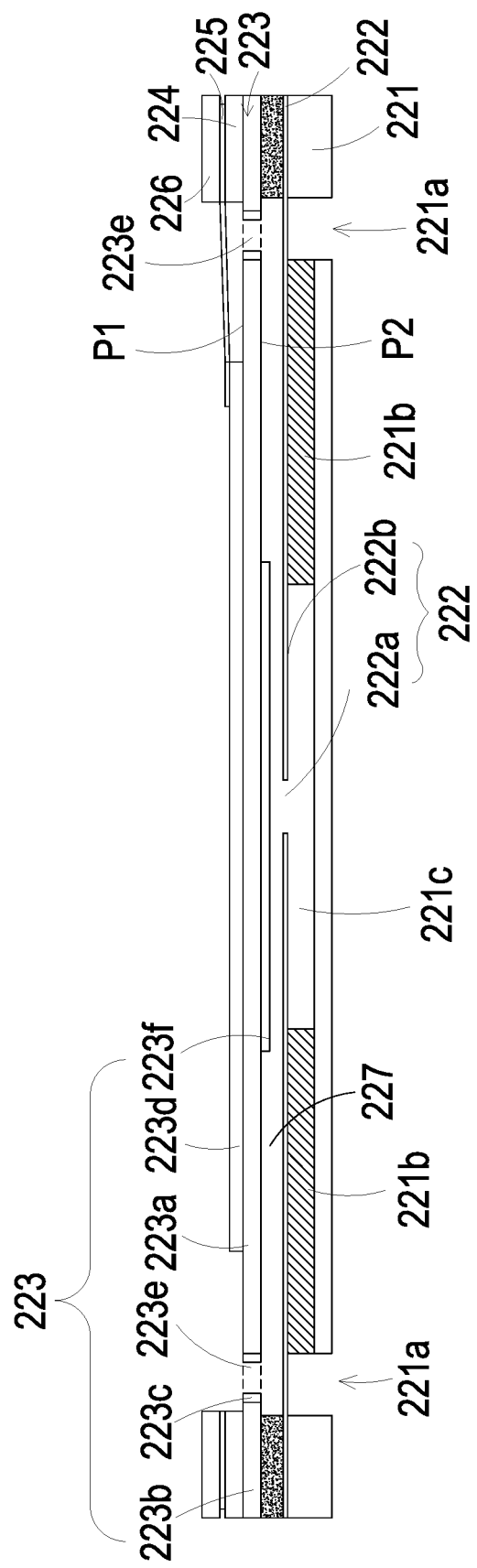
FIG. 7A is a schematic cross-sectional view illustrating the gas transporting actuator of FIG. 6A.
Figure 7B:
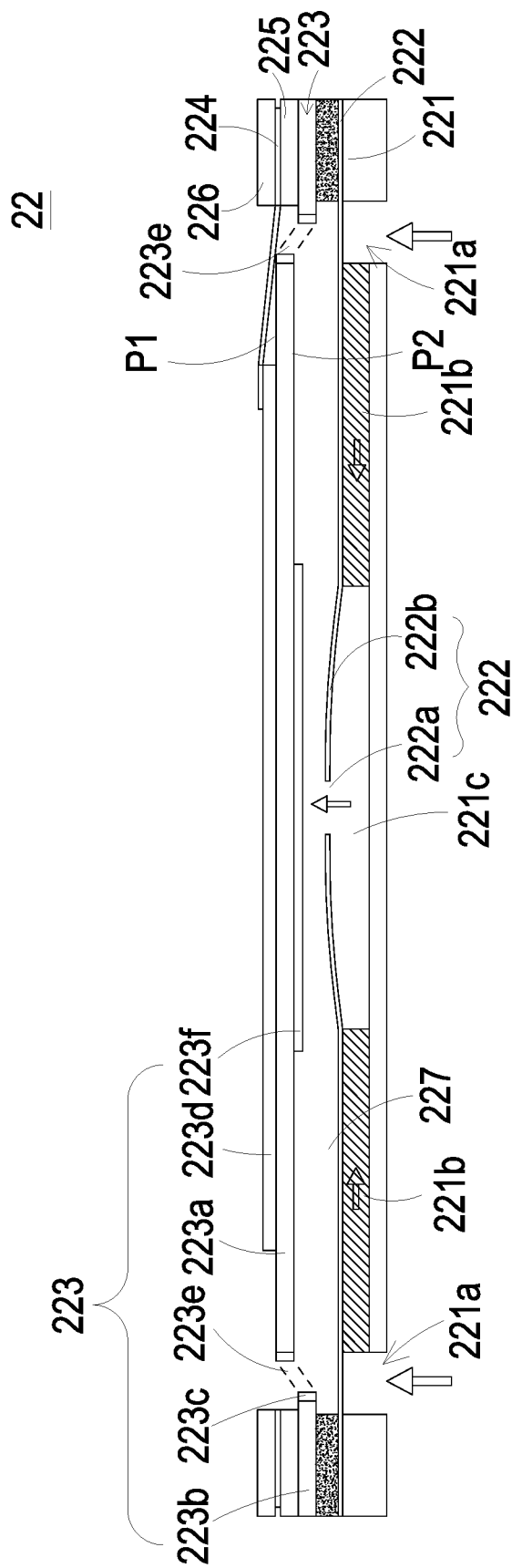
FIGS. 7B to 7D are schematic views illustrating the actions of the second gas transporting actuator of FIG. 7A.
Figure 7C:
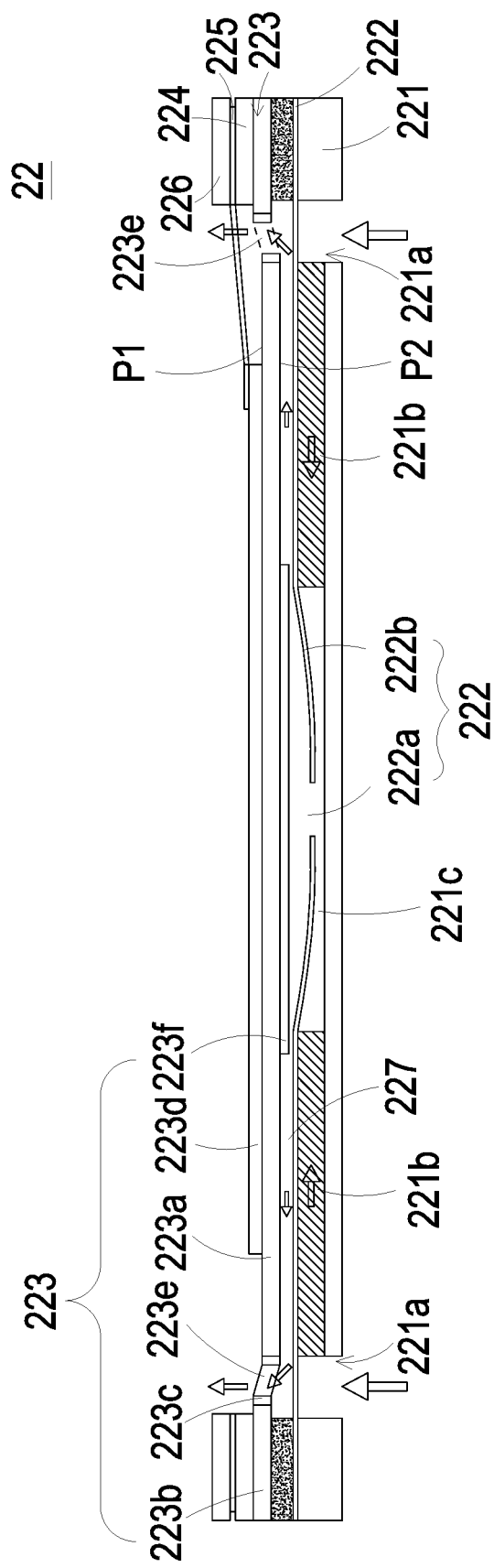
Figure 7D:
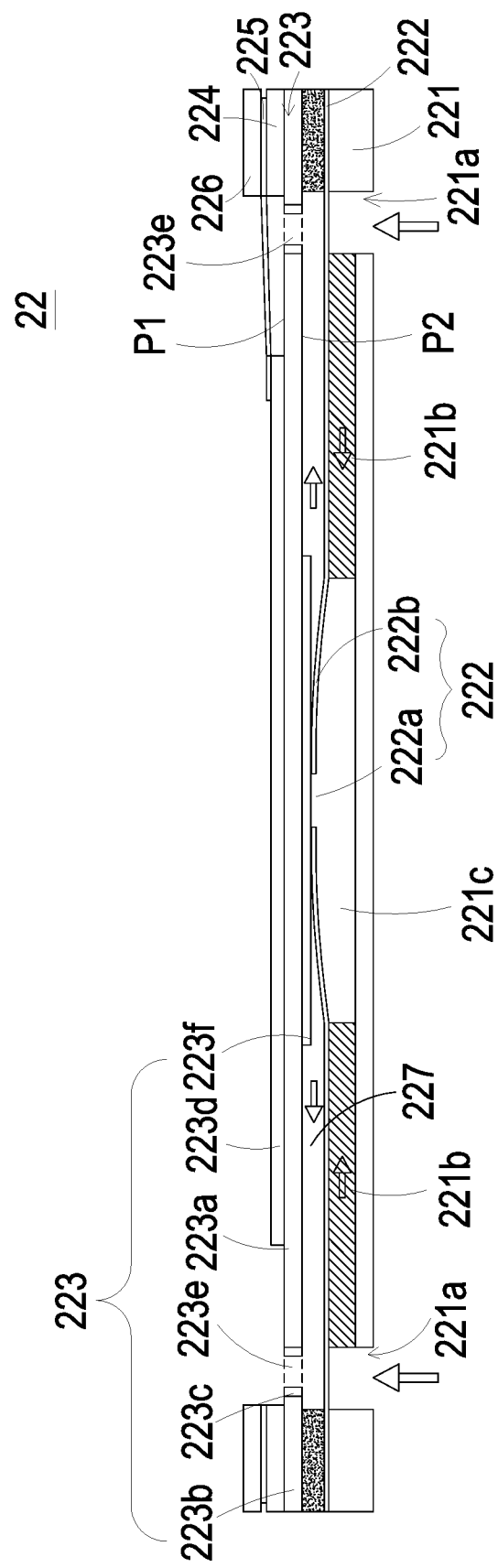

Please refer to FIGS. 3B, 6A, 6B and 7A to 7D. FIGS. 6A and 6B are exploded views illustrating the gas transporting actuator according to the second embodiment of the present disclosure. FIG. 7A is a schematic cross-sectional view illustrating the gas transporting actuator of FIG. 6A. FIGS. 7B to 7D are schematic views illustrating the actions of the second gas transporting actuator of FIG. 7A. In the embodiment, the gas transporting actuator 22 includes a gas inlet plate 221, a resonance plate 222, a piezoelectric actuator 223, a first insulation plate 224, a conducting plate 225 and a second insulation plate 226, which are stacked and assembled sequentially. The gas inlet plate 221 has at least one inlet aperture 221a, at least one convergence channel 221b and a convergence chamber 221c. The convergence channel 221b is aligned with the inlet aperture 221a. In the embodiment, the numbers of the inlet apertures 221a and the convergence channels 221b are four, respectively, but not limited thereto. The convergence channel 221b has an end in fluid communication with the corresponding inlet aperture 221a and another end in fluid communication with the convergence chamber 221c. The inlet aperture 221a allows the air to flow in and the convergence channel 221b guides the air from the inlet aperture 221a toward the convergence chamber 221c. The resonance plate 222 has a central aperture 222a and a movable part 222b. The central aperture 222a is vertically aligned with the convergence chamber 221c. The movable part 222b surrounds the central aperture 222a. The piezoelectric actuator 223 is aligned with the resonance plate 222 and includes a suspension plate 223a, an outer frame 223b, at least one connection component 223c and a piezoelectric element 223d. The outer frame 223b is arranged around the suspension plate 223a. The connection component 223c is connected between the outer frame 223b and the suspension plate 223a for elastically supporting the suspension plate 223a. Moreover, at least one vacant space 223e is formed among the connection components 223c, the outer frame 223b and the suspension plate 223a. The suspension plate 223a has a first surface P1 and a second surface P2. The piezoelectric element 223d is attached on the first surface P of the suspension plate 223a and has a square structure. A length of a side of the piezoelectric element 223d is smaller than or equal to a length of a side of the suspension plate 223a. The suspension plate 223a has a bulge 223f disposed on a second surface P2 thereof. The suspension plate 223a of the piezoelectric element 223 is disposed separately from the resonance plate 222 through the outlet frame 223b to form a chamber 227 among the suspension plate 223a of the piezoelectric actuator 223, the outlet frame 223b and the resonance plate 222. In addition, the first insulation plate 224, the conducting plate 225 and the second insulation plate 226 are stacked sequentially on the piezoelectric actuator 223.

As shown in FIG. 7B, when the piezoelectric element 223d of the piezoelectric actuator 223 is actuated by an applied voltage, the piezoelectric element 223d is deformed by the piezoelectric effect, and the suspension plate 223a is driven to vibrate upwardly. Thereby, the movable part 222b of the resonance plate 222 is simultaneously driven to vibrate upwardly due to the Helmholtz resonance effect. Since the moveable part 222b vibrates upwardly, the volume of the convergence chamber 221c is expended and the air is inhaled into the convergence chamber 221c through the inlet aperture 221a. Please refer to FIG. 7C. The gas transporting actuator 22 is continuously actuated and the suspension plate 223a of the piezoelectric actuator 223 vibrates downwardly. Thereby, the movable part 222b of the resonance plate 222 is simultaneously driven to vibrate downwardly and the volume of the convergence chamber 221c is shrunken. The air is transported from the convergence chamber 221c to the chamber 227 formed between the piezoelectric actuator 223 and the resonance plate 222, pushed to the periphery by the bulge 223f of the suspension plate 223a, and discharged out through the vacant space 223e. Finally, as shown in FIG. 7D, the suspension plate 223a vibrates upwardly to the initial position and the volume of the chamber 227 is shrunken while the movable part 222b of the resonance plate 222 is displaced upwardly. The air is discharged through the periphery and the vacant space 223e. Since the volume of the convergence chamber 221c is expanded again, the air is inhaled through the inlet aperture 221a continuously. Repeating the above actions, the air is inhaled through the inlet aperture 221a and discharged though the vacant space 223e to achieve the gas transportation.

Figure 8:
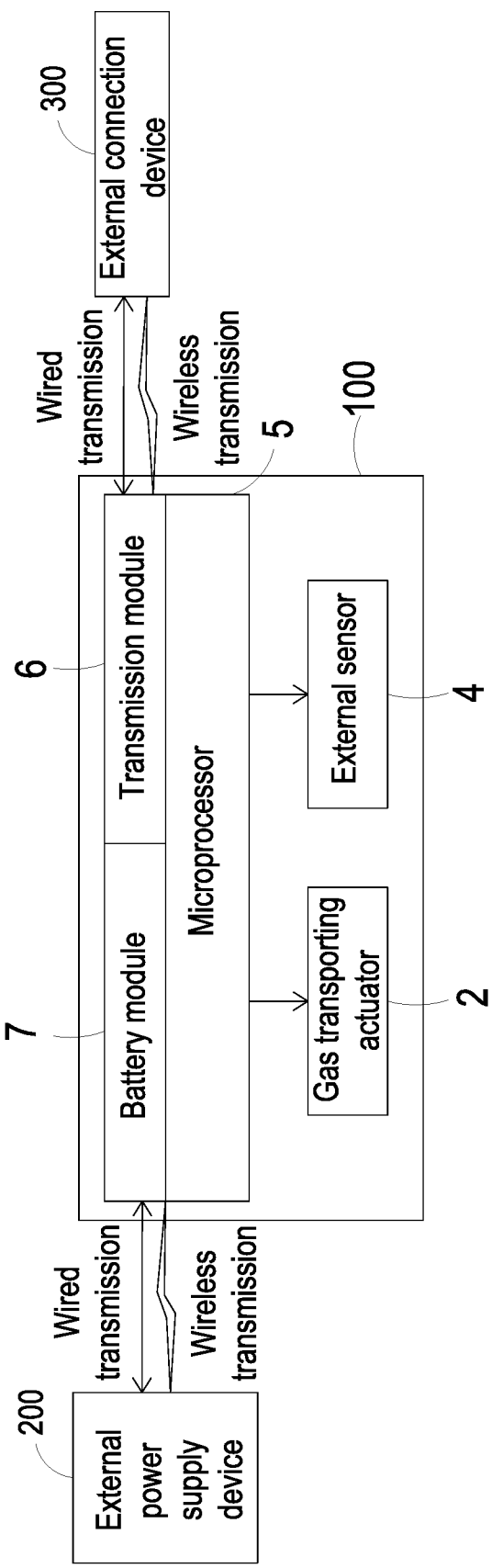
FIG. 8 is a block diagram of the gas detecting device of the present disclosure.

Please refer to FIGS. 2 and 8. The gas detecting device 100 further includes a microprocessor 5, a transmission module 6 and a battery module 7. The microprocessor 5 is electrically connected to the battery module 7, the transmission module 6, the gas transporting actuator 2 and the valve 3 to control the actuation of the gas transporting actuator 2. The external sensor 4 is assembled in the connection channel 14, and is electrically connected to and in data communication with the microprocessor 5. Therefore, detected results from the sensor of the external sensor 4 can be analyzed, calculated, stored and converted into detected values by the microprocessor 5. When the microprocessor 5 actuates the gas transporting actuator 2, the gas transporting actuator 2 starts to inhale the air and transport the air into the branch channel 13 and the connection channel 14. In that, the sensor of the external sensor 4 disposed in the connection channel 14 starts to detect the air contained in the connection channel 14 to obtain concentrations of the gases in the air and transmit the detected results to the microprocessor 5. The detected results are analyzed and converted into the detected values by the microprocessor 5 and the detected values are stored in the microprocessor 5. The detected values stored in the microprocessor 5 are transmitted to an external connection device 300 by the transmission module 6, so that information carried by the detected values are displayed, stored and transmitted through the external connection device and a notification alert is issued. The external connection device 300 can be at least one selected from the group consisting of a cloud system, a portable device, a computer system, a display device and combinations thereof.

In addition, the transmission module 6 can be at least one selected from the group consisting of a wired transmission module and a wireless transmission module, so as to achieve the transmission with the external connection device 300. In an embodiment, the transmission module 6 can be the wired transmission module and selected from the group consisting of a USB transmission module, a mini-USB transmission module, a micro-USB transmission module and combinations thereof. In another embodiment, the transmission module 6 can be the wireless transmission module and selected from the group consisting of a Wi-Fi transmission module, a Bluetooth transmission module, a radio frequency identification transmission module, a near field communication transmission module and combinations thereof.

As mentioned above, the battery module 7 is used to store electrical energy and output the electrical energy, so that the electrical energy is provided to the microprocessor 5 to drive the gas transporting actuator 2, the transmission module 6, the valve 3 and the sensor of the external sensor 4 to actuate. Moreover, the battery module 7 is electrically connected to an external power supply device 200 to receive electrical energy for storage. The external power supply device 200 can transmit the electrical energy to the battery module 7 by means of a wired transmission technology or transmit the electrical energy to the battery module 7 by a wireless transmission technology, but not limited thereto.

Figure 9A:
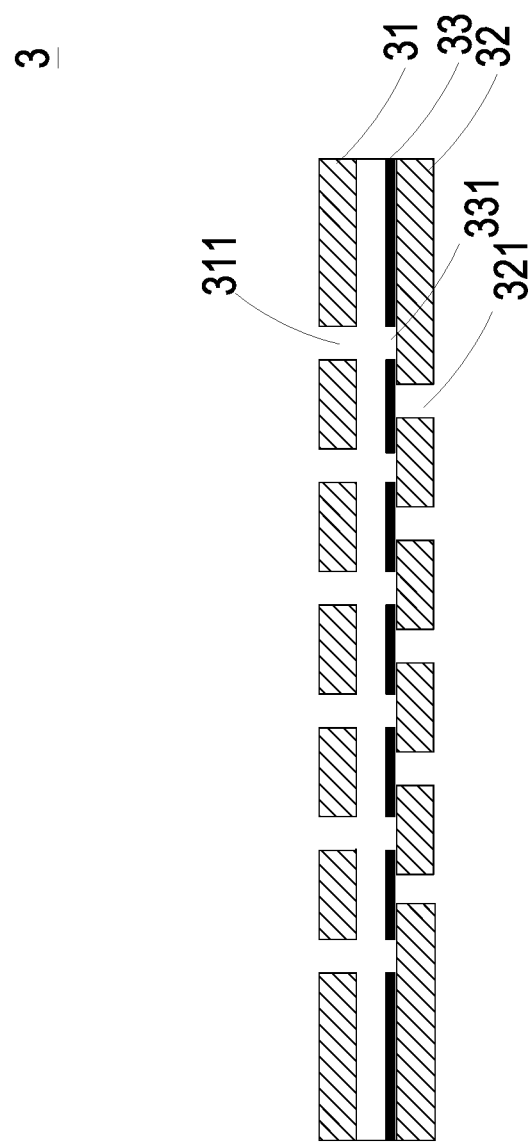
FIGS. 9A and 9B are schematic cross-sectional views illustrating the actions of the valve used in the gas detecting device according to an embodiment of the present disclosure.

Please refer to FIGS. 2 and 9A. In the embodiment, the valve 3 includes a stationary component 31, a sealing component 32 and a displacement component 33. The displacement component 33 is disposed between the stationary component 31 and the sealing component 32. The stationary component 31 has a plurality of first orifices 311. The displacement component 33 has a plurality of second orifices 331 respectively corresponding in position to the plurality of first orifices 311 of the stationary component 31. That is, the plurality of first orifices 311 of the stationary component 31 are aligned with the plurality of second orifices 331 of the displacement component 33. The sealing component 32 has a plurality of third orifices 321. The plurality of third orifices 321 of the sealing component 32 are misaligned with the plurality of first orifices 311 of the stationary component 31.

Figure 9B:
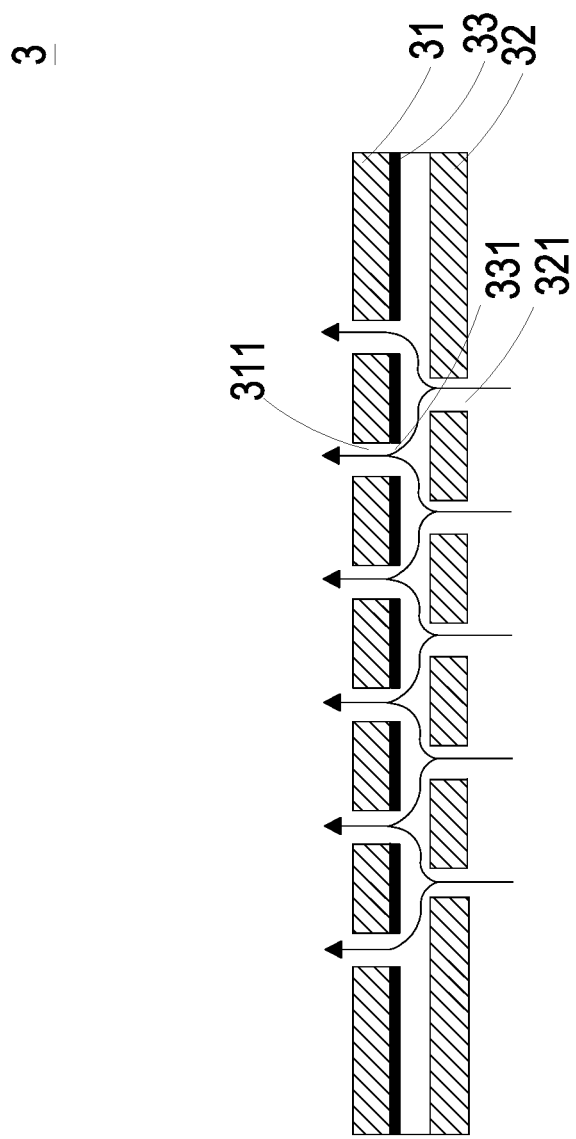

Please refer to FIGS. 9A and 8. In a first aspect of the valve 3 in the present disclosure, the displacement component 33 is made of a charged material, and the stationary component 31 is made of a bipolar conductive material. In case that the displacement component 33 and the stationary component 31 are controlled by the microprocessor 5 to maintain in the same polarity, the displacement component 33 moves toward the sealing component 32 so that the valve 3 is in a closed state. Please refer to FIG. 9B. The displacement component 33 is made of a charged material, and the stationary component 31 is made of a bipolar conductive material. In case that the displacement component 33 and the stationary component 31 are controlled by the microprocessor 5 to maintain in opposite polarity, the displacement component 33 moves toward the stationary component 31 so that the valve 3 is in an open state. According to the above descriptions, it is understood that by adjusting the polarity of the stationary component 31, the displacement member 33 is moved to switch the valve 3 between the open state and the closed state. Since the microprocessor 5 is electrically connected to the valve 3, the polarity of the stationary component 31 can be controlled by the microprocessor 5.

In a second aspect of the valve 3 in the present disclosure, the displacement component 33 is made of a magnetic material, and the stationary component 31 is made of an electromagnet material and can be controlled to change its magnetic polarity. When the displacement component 33 and the stationary component 31 are controlled by the microprocessor 5 to maintain in the same polarity, the displacement component 33 moves toward the sealing component 32 so that the valve 3 is in a closed state. Alternatively, when the displacement component 33 and the stationary component 31 are controlled by the microprocessor 5 to maintain in opposite polarity, the displacement component 33 moves toward the stationary component 31 so that the valve 3 is in an open state. According to the above descriptions, it is understood that by adjusting the polarity of the stationary component 31, the displacement member 33 is moved to switch the valve 3 between the open state and the closed state. The polarity of the stationary component 31 can be controlled by the microprocessor 5.

In summary, the present disclosure provides a gas detecting device. By separately setting a plurality of gas transporting actuators in the different branch channels of the gas detecting device, the air contained in the convergence chamber is transported into the branch channel and the connection channel, so that the external sensor in the connection channel can detect the air flowing into the connection channel and obtain the air quality information. The external sensor is detachably assembled in the connection channel, so that the user can easily replace the required sensor according to the particle requirements.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A gas detecting device comprising:
   a casing having an airflow chamber, at least one inlet, a plurality of branch channels and a plurality of connection channels, wherein the airflow chamber is in fluid communication with the exterior of the casing through the at least one inlet, the plurality of branch channels are in fluid communication with the airflow chamber, and the plurality of connection channels are in fluid communication with the corresponding one of the plurality of branch channels, respectively;
   a plurality of gas transporting actuators respectively disposed in the corresponding one of the plurality of branch channels, wherein the plurality of gas transporting actuators are actuated to inhale air into the airflow chamber through the at least one inlet and transport the air into the plurality of branch channels;
   at least one valve disposed between the plurality of connection channels and the plurality of branch channels to control the air to flow into the plurality of connection channels; and
   at least one external sensor detachably assembled in the plurality of connection channels and comprising a sensor to measure the air in the plurality of connection channels.

2. The gas detecting device according to claim 1, wherein the casing comprises at least one partition plate and each of the plurality of gas transporting actuators comprises: a nozzle plate having a plurality of brackets, a suspension plate and a central aperture, wherein the suspension plate is permitted to undergo a bending vibration, the plurality of brackets are sleeved and fixed on the at least one partition plate to position the nozzle plate within the at least one branch channel, and at least one vacant space is defined by the plurality of brackets, the suspension plate and the partition plate; a chamber frame stacked on the suspension plate; an actuator stacked on the chamber frame, wherein the actuator is configured to bend and vibrate in a reciprocating manner in response to an applied voltage; an insulation frame stacked on the actuator; and a conducting frame stacked on the insulation frame; wherein a resonance chamber is defined by the actuator, the chamber frame and the suspension plate collaboratively, wherein by driving the actuator to drive the nozzle plate to generate a resonance, the suspension plate of the nozzle plate vibrates and displaces in a reciprocating manner, so as to make the air flow through the at least one vacant space into the branch channel and achieve air transportation at high speed.

3. The gas detecting device according to claim 2, wherein the actuator comprises:
   a piezoelectric carrying plate stacked on the chamber frame;
   an adjusting resonance plate stacked on the piezoelectric carrying plate; and
   a piezoelectric plate stacked on the adjusting resonance plate, wherein the piezoelectric plate is configured to drive the piezoelectric carrying plate and the adjusting resonance plate to bend and vibrate in the reciprocating manner in response to the applied voltage.

4. The gas detecting device according to claim 1, wherein each of the plurality of gas transporting actuators comprises: a gas inlet plate having at least one inlet aperture, at least one convergence channel and a convergence chamber, wherein the at least one convergence channel is aligned with the at least one inlet aperture, and the at least one inlet aperture allows the air to flow in and the convergence channel guides the air from the inlet aperture toward the convergence chamber; a resonance plate having a central aperture and a movable part, wherein the central aperture is aligned with the convergence chamber and the movable part surrounds the central aperture; and a piezoelectric actuator aligned with the resonance plate, wherein a chamber is formed between the resonance plate and the piezoelectric actuator, so that the air from the at least one inlet aperture of the gas inlet plate is converged to the convergence chamber along the at least one convergence channel and flows into the chamber through the central aperture of the resonance plate when the piezoelectric actuator is driven, whereby the air is further transported through a resonance between the piezoelectric actuator and the movable part of the resonance plate.

5. The gas detecting device according to claim 4, wherein the piezoelectric actuator comprises:
   a suspension plate having a first surface and a second surface, wherein the suspension plate is permitted to undergo a bending vibration;
   an outer frame arranged around the suspension plate;
   at least one connection component connected between the suspension plate and the outer frame for elastically supporting the suspension plate; and
   a piezoelectric element, wherein a length of a side of the piezoelectric element is smaller than or equal to a length of a side of the suspension plate, and the piezoelectric element is attached on the first surface of the suspension plate to drive the suspension plate to undergo the bending vibration in response to an applied voltage.

6. The gas detecting device according to claim 4, wherein each of the plurality of gas transporting actuators comprises a conducting plate, a first insulation plate and a second insulation plate, and the gas inlet plate, the resonance plate, the piezoelectric actuator, the first insulation plate, the conducting plate and the second insulation plate are stacked and assembled sequentially.

7. The gas detecting device according to claim 1, further comprising a microprocessor and a transmission module, wherein the microprocessor is used to control the transmission module, each of the plurality of gas transporting actuators and the at least one valve to actuate, and the sensor of the at least one external sensor assembled in the plurality of connection channels is electrically connected to and in data communication with the microprocessor, wherein detected results from the sensor are analyzed and converted into detected values by the microprocessor, and the transmission module transmits the detected values to an external connection device so that information carried by the detected values are displayed, stored and transmitted through the external connection device and a notification alert is issued.

8. The gas detecting device according to claim 7, wherein the transmission module is at least one selected from the group consisting of a wired transmission module and a wireless transmission module.

9. The gas detecting device according to claim 7, wherein the external connection device is at least one selected from the group consisting of a cloud system, a portable device, a computer system and combinations thereof.

10. The gas detecting device according to claim 7, further comprising a battery module for storing electrical energy and outputting electrical energy, so that the electrical energy is provided to the microprocessor to drive the transmission module, each of the plurality of gas transporting actuators, the at least one valve and the sensor of the at least one external sensor to actuate, wherein the battery module is electrically connected to an external power supply device to receive electrical energy for storage.

11. The gas detecting device according to claim 10, wherein the power supply device transmits the electrical energy to the battery module by a means selected from the group consisting of a wired transmission technology and a wireless transmission technology.

12. The gas detecting device according to claim 7, wherein the at least one valve comprises a stationary component, a sealing component and a displacement component, wherein the displacement component is disposed between the stationary component and the sealing component, the stationary component has a plurality of first orifices, the displacement component has a plurality of second orifices, and the sealing component has a plurality of third orifices, wherein the plurality of the first orifices of the stationary component are aligned with the plurality of the second orifices of the displacement component, and the plurality of the third orifices of the sealing component are misaligned with the plurality of the first orifices of the stationary component, wherein the displacement component is controlled to move toward the stationary component by the microprocessor so that the valve is in an open state.

13. The gas detecting device according to claim 12, wherein the displacement component is made of a charged material, and the stationary component is made of a bipolar conductive material, wherein the displacement component and the stationary component are controlled by the microprocessor to maintain in opposite polarity, and the displacement component moves toward the stationary component so that the valve is in an open state.

14. The gas detecting device according to claim 12, wherein the displacement component is made of a charged material, and the stationary component is made of a bipolar conductive material, wherein the displacement component and the stationary component are controlled by the microprocessor to maintain in the same polarity, and the displacement component moves toward the sealing component so that the valve is in a closed state.

15. The gas detecting device according to claim 12, wherein the displacement component is made of a magnetic material, and the stationary component is made of an electromagnet material whose magnetic polarity is changeable under control, wherein the displacement component and the stationary component are controlled by the microprocessor to maintain in opposite polarity, and the displacement component moves toward the stationary component so that the valve is in an open state.

16. The gas detecting device according to claim 12, wherein the displacement component is made of a magnetic material, and the stationary component is made of an electromagnet material whose magnetic polarity is changeable under control, wherein the displacement component and the stationary component are controlled by the microprocessor to maintain in the same polarity, and the displacement component moves toward the sealing component so that the valve is in a closed state.

17. The gas detecting device according to claim 1, wherein the sensor of the at least one external sensor comprise at least one selected from the group consisting of an oxygen sensor, a carbon monoxide sensor, a carbon dioxide sensor, a temperature sensor, a humidity sensor and combinations thereof.

18. The gas detecting device according to claim 1, wherein the sensor of the at least one external sensor is a volatile organic compound sensor.

19. The gas detecting device according to claim 1, wherein the sensor of the at least one external sensor is at least one selected from the group consisting of a bacterial sensor, a virus sensor, a microorganism sensor, and combinations thereof.

* * * * *